United States Patent [19]

Erickson

[11] 4,035,368

[45] July 12, 1977

[54] SUBSTITUTED 3-(1H-TETRAZOL-5-YL)-QUINOLINE COMPOUNDS

[75] Inventor: Edward H. Erickson, Woodbury, Minn.

[73] Assignee: Riker Laboratories, Inc., Northridge, Calif.

[21] Appl. No.: 564,557

[22] Filed: Apr. 2, 1975

[51] Int. Cl.$^2$ .................................. C07D 401/04
[52] U.S. Cl. .............. 260/288 CE; 260/283 S; 260/283 SA; 260/283 CN; 260/283 SY; 260/289 H; 424/258
[58] Field of Search ... 260/288 CE, 283 S, 283 SA, 260/287 H

[56] References Cited

U.S. PATENT DOCUMENTS

| | | | |
|---|---|---|---|
| 2,719,848 | 10/1955 | Geschickter et al. | 260/287 H |
| 3,178,348 | 4/1965 | Bickerton | 260/287 H |
| 3,427,324 | 2/1969 | Fitzmaurice | 260/340.7 |
| 3,706,768 | 12/1972 | Bays | 260/335 |
| 3,839,339 | 10/1974 | Ellis et al. | 260/308 D |

OTHER PUBLICATIONS

Holland et al., J. Med. Chem., vol. 10, p. 149–154, (1967).
Juby et al., J. Med. Chem. vol. 11, p. 111–117, (1968).
Juby et al., J. Med. Chem., vol. 12, p. 396–401, (1969).
Buchanan et al., J. Med. Chem. vol. 12, p. 1001–1006, (1969).

*Primary Examiner*—Donald G. Daus
*Assistant Examiner*—Mary C. Vaughn
*Attorney, Agent, or Firm*—Cruzan Alexander; Donald M. Sell

[57] ABSTRACT

Substituted 4-hydroxy-3-(1H-tetrazol-5-yl)-quinoline compounds are prepared by reacting substituted 3-cyano-4-hydroxyquinolines with sodium azide to provide useful anti-allergic compounds.

5 Claims, No Drawings

SUBSTITUTED 3-(1H-TETRAZOL-5-YL)-QUINOLINE COMPOUNDS

BACKGROUND OF THE INVENTION

Various substituted tetrazoles are known, including the compound 3-(1H-tetrazol-5-yl)quinoline, reported in J. Med. Chem. 10, 149 (1967). However, no compounds wherein a tetrazole ring is substituted by a 3-(4-hydroxyquinolyl) group are believed to have been known prior to the present invention, nor has the antiallergic activity of the compounds of the present invention been recognized.

DETAILED DESCRIPTION OF THE INVENTION

This invention relates to physiologically active compounds of the formula

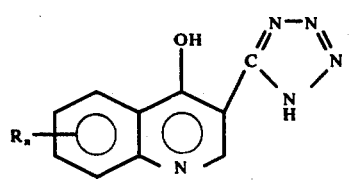

(I)

wherein R is halogen, lower alkyl, lower alkoxy, lower alkylthio, lower alkylsulfinyl, lower alkylsulfonyl or trifluoromethyl and $n$ is zero, one or two.

The term "lower" as used herein with reference to alkyl or alkyl chain-containing groups means that these groups contain from one to four carbon atoms, which may be in straight or branched configuration.

Presently preferred compounds of the invention are those wherein R is fluorine, chlorine and bromine, particularly chlorine or fluorine.

Compounds of the invention are prepared by well-known procedures, for example, by reacting an R-substituted 3-cyano-4-hydroxyquinoline with sodium azide to form the tetrazole ring bonded to the 3-position of the quinoline ring from the 5-position of the tetrazole ring. This reaction occurs readily under anhydrous conditions in inert polar organic solvents such as N,N-dialkylamides, e.g. N,N-dimethylformamide, N,N-dimethylacetamide and the like. Commonly an ammonium salt, e.g. ammonium chloride, is added to the reaction mixture in approximately equimolar amount. The products, which are high-melting substances, usually melting at temperatures above 260° C., commonly precipitate from the solvent, for example, upon the addition of water, and are conveniently isolated by filtration.

The reaction is usefully carried out at elevated temperatures of 75° to 200° C., and preferably at about 100° to 150° C. Reaction time for maximum yield is directly related to reaction temperature, and longer reaction times are required at lower temperatures. Practically useful reaction times range from one to 30 hours.

Aluminum azide can be used instead of sodium azide.

Some of the R-substituted 3-cyano-4-hydroxyquinolines which are intermediates used to prepare the compounds of the invention are themselves believed to be novel compounds which can be prepared readily from known starting materials. They have the formula

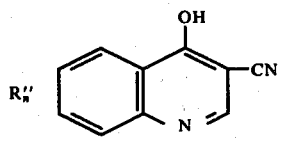

(II)

wherein R" is halogen, lower alkyl, lower alkylthio, lower alkylsulfinyl, lower alkylsulfonyl or trifluoromethyl and n is one or two.

The preparative method employed for these intermediates is that described in J. Am. Chem. Soc. 68, 1951 (1946). Aniline and ring-substituted anilines react with ethyl ethoxymethylenecyanoacetate to provide good yields of correspondingly substituted 3-cyano-4-hydroxyquinolines. This reaction is carried out in a solvent which is inert or relatively inert with respect to the reagents used in the reaction. Suitable solvents are those which are relatively high boiling, for example in the range of 150° to 300° C., e.g. diphenyl ether, biphenyl, mineral oil, dialkyl sulfones, tetramethylene sulfone and the like.

Reaction times employed are generally from one to 20 hours.

The new compounds of the invention of formula (I) have been shown to inhibit the release and/or synthesis and/or effect of biochemical products brought on in the mammalian organism by the combination of certain types of antibody and specific antigen. In man, both subjective and objective changes which result from the inhalation of specific antigen by sensitized subjects may be markedly inhibited by administration of the new compounds. The new compounds. The new compounds are useful in the treatment of so-called "intrinsic" asthma (in which no sensitivity to extrinsic antigen can be demonstrated) or any condition in which non-specific factors trigger the release of allergic mediators and in the treatment of other conditions in which antigen-antibody reactions are responsible for disease, for example, extrinsic asthma, urticaria, hay fever, food allergies, allergic conjunctivitis, allergic rhinitis, atopic dermatitis and auto-immune diseases.

A further embodiment of the invention, therefore, is a pharmaceutical composition comprising a compound of formula (I) in association with a pharmaceutically acceptable carrier or diluent.

The nature of the composition and the pharmaceutically acceptable carrier or diluent will, of course, depend upon the desired mode of administration, which may be, for example, orally, by inhalation, parenterally or by topical application.

The pharmaceutical composition of the invention may be formulated in the conventional manner with the customary ingredients. For example, the compositions, may be put up as aqueous solutions or suspensions. as dry powders or in tablet, cream, location or syrup form.

The compositions of the invention generally comprise a minor proportion of the compound of formula (I) and a major proportion of carrier or diluent. Thus, for example, aqueous solutions for administration by means of a conventional nebulizer may contain up to about 100 percent by weight of the active ingredient in sterile water; and compositions for dispensing from a pressurized container comprising suspensions or solutions in liquified propellants will contain, for example, about 0.2 to 5 percent by weight of the active ingredient.

The compounds of formula (I) are preferably administered orally or by inhalation, notably in the treatment of allergic asthma. For such use, the compounds of formula (I), e.g. suspended in an aqueous pharmaceutically acceptable suspending medium may be applied by means of a conventional nebulizer. However, the administration of medicaments by means of a pressurized dispensing container, i.e., an aerosol dispenser, is an alternative to nebulizer administration.

For administration from an aerosol dispenser the medicament is dissolved or suspended in a liquified propellant medium. The propellants for present use may be any of those which are conventionally used in formulations for dispensing from pressurized containers. Commonly these are of the halogenated hydrocarbon type such as fluoro- or fluorohalo- hydrocarbons, and mixtures of these with other propellants. Typical suitable propellants are disclosed in U.S. Pat. No. 2,868,691, and are available commercially under the trade name Freon. Preferred propellants of low toxicity are difluorodichloromethane, dichlorotetrafluoroethane or mixtures thereof.

Where the medicament is not soluble in the propellent, it may be necessary to add a surface-active agent to the composition in order to suspend the medicament in the propellant medium, and such surface-active agents may be any of those commonly used for this purpose, such as non-ionic surface-active agents. The use of such surface-active agents and the advantages which stem therefrom are more fully described in British Patent Specification No. 1,063,512.

The compositions of the invention may also be administered in the form of powder by means of an insufflator device of the conventional type. In order to improve the properties of the powder for this purpose it is useful to modify the surface characteristics of the powder particles, for example by coating them with a pharmaceutically acceptable material such as sodium stearate. Also, finely divided powders of the active ingredients may be mixed with a coarser pharmaceutical diluent material such as lactose, which may be present in a smaller, equal or greater amount than the active ingredients, for example in from 50 to 150 percent by weight of the compound of formula (I) and such other active ingredients as may be present.

The compounds of the invention may also be administered by dispensers from which meters amounts of the compund are discharged in a state to be orally received during inhalation wherein the propellant is compressed air or other compressed inert gas such as nitrogen, argon and the like.

Whilst the inhalation of medicament has been described above with particular reference to oral administration, it will be appreciated that it may be desirable to administer the medicament nasally. The term inhalation is therefore used herein to denote, where the context permits, both oral and nasal administration.

The compositions of the invention may also be adminstrated in tablets, syrups and the like or by intradermal or intravenous injection in the conventional manner.

The compounds of formula (I) may also find use in the treatment of allergic eye conditions, for example that associated with hay fever, i.e. allergic conjunctivitis. For such use the compound of formula (I) may be used in the form of an eye drop and/or spray as an isotonic aqueous solution containing about 2 percent of the compound and a preservative.

In addition to the internal administration, the compounds of formula (I) find use in compositions for topical application, e.g. to the mucous membranes in the form of sprays or ointments.

In addition to the compound of formula (I) and the ingredients required to present the compound in a form suitable for the selected mode of administration, other active ingredients may be present in the compositions of the invention. Thus, in compositions for administration by inhalation, it may be beneficial to include a bronchodilator. Any bronchodilator may, within reason, be used. Suitable bronchodilators include those known to the art such as isoprenaline, adrenaline, orciprenaline, isoetharine and derivatives thereof, particularly the salts thereof. The amount of bronchodilator used will vary over a broad range, depending, inter alia, upon the nature and activity of the bronchodilator and the compound of formula (I) used. However, the use of a minor proportion (i.e. less than 50 percent by weight) of the bronchodilator is preferred. The use of from 0.1 to 10 percent by weight of the bronchodilator based on the weight of the compound of formula (I) is particularly preferred.

Thus another embodiment of the invention is a composition which comprises a compound of formula (I) or a derivative thereof in admixture with a bronchodilator, which latter is preferably present in less than 50 percent, especially 0.1 to 10 percent by weight of the former.

As indicated above, the compounds of formula (I) are indicated for use in inhibiting the effects of antibodyantigen reactions in mammals. In such treatment, the compound or composition of the invention is administered by the chosen method to the site of the antibody-antigen reaction in the therapeutically effective amount. Thus, individual doses of 0.1 to 10 mg/kg are given. The course of treatment may require repeated dosages of the medicament at regular intervals. The amount of medicament administered and frequency of administration will depend upon many factors, and no concise dosage rate or regimen can be generally stated. However, as a general guide, where the compounds are administered by inhalation to a patient suffereing from acute allergic asthma, therapeutically useful results may be achieved when doses of 0.1 to 20 mg/kg are employed. Useful results are obtained when the compounds are administered by the oral route, when larger dosages are given.

The invention thus also provides a method for inhibiting the effects of an antibody-antigen reaction which comprises the prior or subsequent application to the known or unexpected area of the antibody-antigen reaction mechanism of a therapeutically effective amount of a compound of formula (I) or a derivative thereof.

The effectiveness of the compounds of the invention in inhibiting passive cutaneous anaphylaxis in rats was shown by the positive results obtained using a standard test method. The method used was as follows: Sprague-Dawley rats (male or female( having a body weight of about 200 g. were injected intramuscularly with egg albumin and intraperitoneally with *Bordella pertussis* vaccine. Ten to twelve days after this treatment the rats were exsanguinated via the abdominal aorta. The blood was allowed to clot overnight and then centrifuged in order to collect the blood serum containing the antibody.

Another group of Spraque-Dawley rats in the body weight range of 50 to 120 g. was then sensitized to egg albumin by intradermal injection of 0.1 ml. of blood serum containing antibody obtained as described above into the mid-dorsal region. Sensitivity was allowed to develop for 24 hours. Test compounds were administered to sensitized rats either by intraperitoneal injection or orally at predetermined time intervals immediately before challenge by intravenous administration of egg albumin end Evans Blue dye. For each dose level of the compound under test a group of six rats were treated, while six rats remained untreated as controls for each test. The dosages of the compound under test were selected so as to give a range of inhibition values.

After treatment with the selected compound, the rats were challenged by intravenous injection of 1 ml. of a mixture of egg albumin (0.5 mg/ml), Evans Blue dye solution (10 mg/ml) and physiological saline. The challenge dose produces an anaphylactic reaction at the site of injection which is made visible by the blue dye.

Forty-five minutes after injection of egg albumin the rats were killed and the skins removed and reversed. The intensity of the anaphylactic reaction was assessed by comparing the size (i.e. area determined from products from two diameters taken at right angles) of the characteristic blue weal produced by spread of the Evans Blue dye from the sensitization site. Comparison of the size of the weals in the control animals within that of the weals in treated animals allows calculation of the results in terms of percent inhibition, i.e.

$$\frac{(\text{Control group area} - \text{treated group area})}{\text{Control group area}} \times 100$$

If the percentage inhibitions for the various dose levels are plotted graphically for each compound, the dosage required to achieve a 50 percent inhibition of the anaphylactic reaction ($ID_{50}$) may be determined from these graphs.

In this test, most of the compounds of the invention specifically described produced statistically significant inhibition at a dose rate (i.p.) of 10 mg/kg or less; the remainder had significant effect at somewhat higher doses. When given orally, a significant effect was produced in this test by most of these compounds at dose rates of 25 mg/kg or less.

It has been proven that this test method gives reliable qualitative indications of the ability of the compounds under test to inhibit antibody-antigen reactions in man.

Many of the compounds of the invention are phosphodiesterase inhibitors and some have been shown to increase cyclic-AMP levels.

The compounds of the invention have been found to be effective when administered in aerosol form, e.g. a suspension of one percent of the selected compound in aerosol propellant, to dogs and monkeys to protect these animals against an aerosol of an Ascaris extract to which they normally would exhibit an asthma-like response.

The invention may be further illustrated by the following examples, which should not be construed to limit the invention.

EXAMPLE 1

A mixture of 800 ml. of diphenyl ether, 17.2 g. (0.1 mole) of 2-bromoaniline and 16.9 g. (0.1 mole) of ethyl ethoxymethylenecyanoacetate is heated to its reflux temperature and maintained at reflux temperature (about 255° C.) for eight hours. During the first hour a stream of nitrogen is passed over the solution in order to maintain non-oxidizing conditions.

When the reaction mixture is cooled, the product separates as a solid precipitate. It is separated by filtration and washed with diethyl ether to provide tan crystals of 8-bromo3-cyano-4-hydroxyquinoline, m.p. >260° C. Analysis: Calculated for $C_{10}H_5BrN_2O$: %C, 48.2; %H, 2.02; %N, 11.25. Found: %C, 48.2; %H, 2.1; %N, 11.4.

Using the method of Example 1 and using suitably substituted aniline compounds, these are reacted with ethyl ethoxymethylenecyanoacetate to provide intermediate quinoline derivatives as shown in the following table. The reaction proceeds very readily and the products can be used for the further step of reaction with sodium azide without further purification. Due to their generally high melting points (greater than 260° C.) and ease of preparation and utilization, these somewhat crude intermediates were not always further characterized. However, their infrared spectra were examined to confirm the presence of the cyano group (about 220 $cm^{-1}$) and the hydroxy group (32 to 3500 $cm^{-1}$). In some cases elemental analyses were carried out.

| Ex. No. | Starting Aniline | Product Quinoline | Analyses | | |
|---|---|---|---|---|---|
| | | | %C | %H | %N |
| 2 | 2-fluoroaniline | 5-fluoro-3-cyano-4-hydroxyquinoline, m.p. >260° C | C: 63.84, F: 63.9, | 2.68, 2.7, | 14.89 15.1 |
| 3 | 4-chloroaniline | 6-chloro-3-cyano-4-hydroxyquinoline | | | |

-continued

| Ex. No. | Starting Aniline | Product Quinoline | Analyses %C | %H | %N |
|---|---|---|---|---|---|
| 4 | 2-methoxyaniline | 4-hydroxy-8-methoxy-quinoline-3-carbonitrile, m.p. >260° C | C: 66.00, F: 65.8, | 4.03, 4.1, | 13.99 14.0 |
| 5 | 2-ethylaniline | 4-hydroxy-8-ethyl-quinoline-3-carbonitrile | C: 72.71, F: 72.4, | 5.04, 4.9, | 14.13 14.1 |
| 6 | 2-trifluoromethylaniline | 4-hydroxy-8-trifluoromethyl-quinoline-3-carbonitrile | | | |
| 7 | 2-methylsulfonylaniline | 4-hydroxy-8-methylsulfonyl-quinoline-3-carbonitrile | | | |
| 8 | 4-fluoroaniline | 6-fluoro-4-hydroxy-quinoline-3-carbonitrile | | | |
| 9 | 2-isopropylaniline | 4-hydroxy-8-isopropyl-quinoline-3-carbonitrile | | | |
| 10 | 4-ethylaniline | 6-ethyl-4-hydroxy-quinoline-3-carbonitrile | C: 72.71, F: 72.2, | 5.04, 4.9, | 14.13 14.0 |
| 11 | 2,4-difluoroaniline | 6,8-difluoro-4-hydroxy-quinoline-3-carbonitrile | C: 58.26, F: 58.0, | 1.96, 1.9, | 13.59 13.5 |
| 12 | 2-fluoro-4-methylaniline | 8-fluoro-4-hydroxy-6-methyl-quinoline-3-carbonitrile, m.p. >260° C | C: 65.35, F: 65.1, | 3.49, 3.3, | 13.85 13.5 |

| Ex. No. | Starting Aniline | Product Quinoline | Analyses %C | %H | %N |
|---|---|---|---|---|---|
| 13 | 2-chloroaniline | 8-chloro-4-hydroxy-3-cyanoquinoline | C: 58.70, F: 58.8, | 2.46, 2.5, | 13.69 13.9 |
| 14 | 2,5-dichloroaniline | 5,8-dichloro-4-hydroxy-3-cyanoquinoline | C: 50.24, F: 49.8, | 1.69, 1.6, | 11.72 11.8 |
| 15 | 3-ethylaniline | 7-ethyl-4-hydroxy-3-cyanoquinoline | C: 72.71, F: 72.6, | 5.04, 5.1, | 14.13 14.2 |
| 16 | 3-chloroaniline | 7-chloro-4-hydroxy-3-cyanoquinoline | | | |
| 17 | 2-(methylthio)aniline | 8-(methylthio)-4-hydroxy-3-cyanoquinoline, m.p. >260° C | C: 61.09, F: 60.6, | 3.73, 3.8, | 12.95 12.9 |
| 18 | 2-ethoxyaniline | 8-ethoxy-4-hydroxy-3-cyanoquinoline | C: 67.28, F: 67.5, | 4.71, 4.7, | 13.08 13.1 |
| 19 | 3-methoxyaniline | 7-methoxy-4-hydroxy-3-cyanoquinoline | C: 66.00, F: 54.6, | 4.03, 4.1, | 13.99 14.1 |
| 20 | 3-ethylaniline | 7-ethyl-4-hydroxy-3-cyanoquinoline | C: 72.71, F: 72.6, | 5.04, 5.1, | 14.13 14.2 |
| 21 | 2-chloroaniline | 8-chloro-4-hydroxy-3-cyanoquinoline | C: 58.70, F: 58.5, | 2.46, 2.5, | 13.69 13.9 |

-continued

| Ex. No. | Starting Aniline | Product Quinoline | Analyses %C | %H | %N |
|---|---|---|---|---|---|
| 22 | 4-methylaniline | 4-hydroxy-6-methyl-quinoline-3-carbonitrile | C: 71.73, F: 71.6, | 4.38, 4.3, | 15.21 15.3 |
| 23 | 2-methylaniline | 4-hydroxy-8-methyl-quinoline-3-carbonitrile | C: 71.73, F: 71.5, | 4.38, 4.3, | 15.21 15.3 |
| 24 | 2,3-dichloroaniline | 7,8-dichloro-4-hydroxy-quinoline-3-carbonitrile | C: 50.24, F: 49.7, | 1.69, 1.6, | 11.72 11.7 |
| 25 | 2,5-difluoroaniline | 5,8-difluoro-4-hydroxy-quinoline-3-carbonitrile | C: 58.26, F: 58.0, | 1.96, 1.8, | 13.59 13.5 |
| 26 | 2,4-dichloroaniline | 6,8-dichloro-4-hydroxy-quinoline-3-carbonitrile | C: 50.24, F: 50.0, | 1.69, 1.7, | 11.72 11.8 |
| 27 | 2,5-dimethoxyaniline | 5,8-dimethoxy-4-hydroxy-quinoline-3-carbonitrile | C: 62.60, F: 62.3, | 4.38, 4.3, | 12.17 12.0 |
| 28 | 2-isopropoxyaniline | 8-isopropoxy-4-hydroxy-quinoline-3-carbonitrile | C: 68.41, F: 68.4, | 5.30, 5.2, | 12.27 12.2 |
| 29 | 4-fluoro-3-chloroaniline | 6-fluoro-7-chloro-4-hydroxy-quinoline-3-carbonitrile | C: 53.96, F: 53.6, | 1.81, 1.8 | 12.58 12.6 |
|  | 4-fluoro-2-chloroaniline | 6-fluoro-8-chloro-4-hydroxy-quinoline-3-carbonitrile | C: 53.96, F: 54.0, | 1.81, 1.9, | 12.58 12.9 |
|  | 4-methyl-2-methoxyaniline | 5-methoxy-8-methoxy-4-hydroxy-quinoline-3-carbonitrile | C: 62.60, F: 62.4, | 4.38, 4.3, | 12.17 12.1 |

EXAMPLE 32

A mixture of 22 g. (90 mmoles) of 8-bromo-3-cyano-4-hydroxyquinoline (from Example 1), 7.0 g. (108 mmoles) of sodium azide and 6.0 g. (112 mmoles) of ammonium chloride in 300 ml. of N,N-dimethylformamide is heated at a bath termperature of 125° C. for about 16 hours. The mixture is then diluted with 5 percent aqueous hydrochloric acid, filtered and the insoluble product is dried to provide 8-bromo-4-hydroxy-3-(1H-tetrazole-5-yl)quinoline, m.p. >260° C Analysis: Calculated for $C_{10}H_6BrN_5O$: %C, 41.12; %H, 2.07; %N, 23.98. Found: %C, 41.0; %H, 2.0; %N, 23.8.

Using the method of Example 32 various quinolines such as those prepared in earlier examples are reacted with sodium azide to provide two final product compounds described in the following table. These compounds are generally recrystallized from N,N-dimethylformamide or dimethyl sulfoxide.

TABLE I

| Ex. No. | Compound | Melting Point (°C) |
|---|---|---|
| 33 | 8-ethyl-4-hydroxy-3-(1H-tetrazol-5-yl)quinoline<br>Calc: %C, 59.74; %H, 4.60; %N, 29.03<br>Found: %C, 59.4; %H, 4.6; %N, 28.8 | >260 |
| 34 | 6,8-difluoro-4-hydroxy-3-(1H-tetrazol-5-yl)-quinoline<br>Calc: %C, 47.35; %H, 2.19; %N, 27.61<br>Found: %C, 47.0; %H, 2.4; %N, 27.1 | >260 |
| 35 | 8-fluoro-4-hydroxy-3-(1H-tetrazol-5-yl)-quinoline<br>Calc: %C, 52.0; %H, 2.60; %N, 30.3<br>Found: %C, 51.9; %H, 2.8; %N, 29.8 | >260 |
| 36 | 6-chloro-4-hydroxy-3-(1H-tetrazol-5-yl)-quinoline<br>Calc: %C, 48.5; %H, 2.44; %N, 28.28<br>Found: %C, 48.6; %H, 2.2; %N, 28.4 | >260 |
| 37 | 6-fluoro-4-hydroxy-3-(1H-tetrazol-5-yl)-quinoline<br>Calc: %C, 50.0; %H, 2.94; %N, 29.16<br>Found: %C, 50.1; %H, 3.2; %N, 28.7 | >260 |
| 38 | 8-chloro-4-hydroxy-3-(1H-tetrazol-5-yl)-quinoline<br>Calc: %C, 45.99; %H, 2.90; %N, 26.82<br>Found: %C, 45.6; %H, 2.7; %N, 26.7 | >260 |
| 39 | 5,8-dichloro-4-hydroxy-3-(1H-tetrazol-5-yl)-quinoline<br>Calc: %C, 42.58; %H, 1.79; %N, 24.83<br>Found: %C, 42.9; %H, 2.0; %N, 25.1 | >260 |
| 40 | 7-chloro-4-hydroxy-3-(1H-tetrazol-5-yl)-quinoline | >260 |
| 41 | 7-ethyl-4-hydroxy-3-(1H-tetrazole-5-yl)-quinoline<br>Calc: %C, 57.59; %H, 4.83; %N, 27.98<br>Found: %C, 57.1; %H, 4.7; %N, 27.9 | >260 |
| 42 | 6-ethyl-4-hydroxy-3-(1H-tetrazol-5-yl)-quinoline<br>Calc: %C, 56.57; %H, 4.60; %N, 29.03<br>Found: %C, 56.4; %H, 4.8; %N, 29.4 | >260 |
| 43 | 4-hydroxy-8-methoxy-3-(1H-tetrazol-5-yl)-quinoline<br>Calc: %C, 50.92; %H, 4.20; %N, 26.99<br>Found: %C, 51.1; %H, 4.1; %N, 26.7 | >260 |
| 44 | 4-hydroxy-8-trifluoromethyl-3-(1H-tetrazol-5-yl)-quinoline<br>Calc: %C, 46.99; %H, 2.15; %N, 24.91<br>Found: %C, 46.7; %H, 2.0; %N, 24.9 | >260 |
| 45 | 4-hydroxy-8-methylsulfonyl-3-(1H-tetrazol-5-yl)-quinoline<br>Calc: %C, 45.36; %H, 3.11; %N, 24.04<br>Found: %C, 45.21; %H, 2.9; %N, 24.1 | >260 |
| 46 | 4-hydroxy-8-methylthio-3-(1H-tetrazol-5-yl)-quinoline<br>Calc: %C, 50.96; %H, 3.50; %N, 27.01<br>Found: %C, 50.6; %H, 3.6; %N, 26.9 | >260 |
| 47 | 4-hydroxy-8-isopropyl-3-(1H-tetrazol-5-yl)-quinoline<br>Calc: %C, 61.17; %H, 5.13; %N, 27.43<br>Found: %C, 61.1; %H, 5.2; %N, 27.0 | >260 |
| 48 | 4-hydroxy-7-methoxy-3-(1H-tetrazol-5-yl)quinoline<br>Calc: %C, 54.32; %H, 3.73; %N, 28.79<br>Found: %C, 54.1; %H, 3.7; %N, 29.0 | >260 |
| 49 | 4-hydroxy-3-(1H-tetrazol-5-yl)quinoline<br>Calc: %C, 52.98; %H, 3.78; %N, 30.89<br>Found: %C, 53.1; %H, 3.4; %N, 30.9 | >260 |
| 50 | 6-methyl-4-hydroxy-3-(1H-tetrazol-5-yl)quinoline<br>Calc: %C, 55.93; %H, 4.27; %N, 29.64<br>Found: %C, 55.4; %H, 4.2; %N, 29.1 | >260 |
| 51 | 8-methyl-4-hydroxy-3-(1H-tetrazol-5-yl)quinoline<br>Calc: %C, 58.15; %H, 3.99; %N, 30.82<br>Found: %C, 58.0; %H, 4.0; %N, 31.1 | >260 |
| 52 | 8-isopropoxy-4-hydroxy-3-(1H-tetrazol-5-yl)-quinoline<br>Calc: %C, 57.56; %H, 4.83; %N, 25.82<br>Found: %C, 57.6; %H, 4.7; %N, 25.9 | >260 |
| 53 | 7,8-dichloro-4-hydroxy-3-(1H-tetrazol-5-yl)-quinoline<br>Calc: %C, 42.58; %H, 1.79; %N, 24.83<br>Found: %C, 42.8; %H, 1.9; %N, 24.9 | >260 |
| 54 | 6,8-dichloro-4-hydroxy-3-(1H-tetrazol-5-yl)-quinoline<br>Calc: %C, 41.26; %H, 2.08; %N, 24.06<br>Found: %C, 41.0; %H, 2.1; %N, 24.1 . ½ $H_2O$ | >260 |
| 55 | 5,8-difluoro-4-hydroxy-3-(1H-tetrazol-5-yl)-quinoline<br>Calc: %C, 48.20; %H, 2.02; %N, 28.11<br>Found: %C, 48.1; %H, 2.5; %N, 28.2 | >260 |
| 56 | 5,8-dimethoxy-4-hydroxy-3-(1H-tetrazol-5-yl)-quinoline<br>Calc: %C, 52.75; %H, 4.06; %N, 25.63<br>Found: %C, 53.1; %H, 4.2; %N, 25.7 | >260 |
| 57 | 8-fluoro-4-hydroxy-6-methyl-3-(1H-tetrazol-5-yl)-quinoline<br>Calc: %C, 51.97; %H, 3.57; %N, 27.55<br>Found: %C, 51.6; %H, 3.3; %N, 27.4 | >260 |
| 58 | 8-ethoxy-4-hydroxy-3-(1H-tetrazol-5-yl)quinoline<br>Calc: %C, 56.03; %H, 4.31; %N, 27.22<br>Found: %C, 56.2; %H, 4.3; %N, 27.5 | >260 |
| 59 | 6-bromo-8-fluoro-4-hydroxy-3-(1H-tetrazol-5-yl)-quinoline<br>Calc: %C, 39.9; %H, 2.4; %N, 22.2<br>Found: %C, 39.5; %H, 2.3; %N, 22.2 | >260 |
| 60 | 7-chloro-6-fluoro-4-hydroxy-3-(1H-tetrazol-5-yl)-quinoline | >260 |
| 61 | 8-chloro-6-fluoro-4-hydroxy-3-(1H-tetrazol-5-yl)-quinoline | >260 |
| 62 | 6,8-dimethoxy-4-hydroxy-3-(1H-tetrazol-5-yl)-quinoline | >260 |

What is claimed is:

1. A compound of the formula

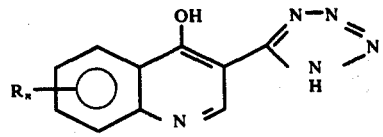

wherein R is halogen, lower alkyl, lower alkoxy, lower alkylthio, lower alkylsulfinyl, lower alkylsulfonyl, trifluoromethyl or lower alkylsulfonamido and n is zero, one or two.

2. A compound according to claim 1 wherein R is halogen, methoxy or lower alkyl and n is one.

3. The compound 8-chloro-4-hydroxy-3-(1H-tetrazol-5-yl)quinoline according to claim 1.

4. The compound 4-hydroxy-8-methoxy-3-(1H-tetrazol-5-yl)quinoline according to claim 1.

5. The compound 6-fluoro-4-hydroxy-3-(1H-tetrazol-5-yl)quinoline according to claim 1.

* * * * *